United States Patent [19]

Richard

[11] Patent Number: 5,176,202

[45] Date of Patent: Jan. 5, 1993

[54] METHOD AND APPARATUS FOR USE IN LOW-TEMPERATURE STORAGE

[75] Inventor: Daniel D. Richard, Sedona, Ariz.

[73] Assignee: Cryo-Cell International, Inc., Baldwin, N.Y.

[21] Appl. No.: 670,979

[22] Filed: Mar. 18, 1991

[51] Int. Cl.$^5$ ............................................. F25B 29/00
[52] U.S. Cl. ............................. 165/48.1; 62/63; 62/266; 62/337; 62/448; 422/63; 422/65; 422/67; 435/290; 436/48
[58] Field of Search ................ 165/12, 48.1, 60, 61; 62/63, 65, 266, 337, 448; 435/290, 287; 422/63, 65, 67; 436/47, 48

[56] References Cited

U.S. PATENT DOCUMENTS

| | | | |
|---|---|---|---|
| 1,938,985 | 12/1933 | Starr | 62/63 |
| 2,599,173 | 6/1952 | Hamilton | 194/246 |
| 2,928,705 | 3/1960 | Goldsmith | 312/223 |
| 2,950,605 | 8/1960 | Hennion | 62/250 |
| 3,034,845 | 5/1962 | Haumann | 312/268 |
| 3,100,969 | 8/1963 | Elfving | 62/3.6 |
| 3,141,123 | 7/1964 | Olson | 318/674 |
| 3,564,727 | 2/1971 | Fraser | 34/92 |
| 3,583,171 | 6/1971 | Flynn . | |
| 3,677,335 | 7/1972 | Weatherston | 165/12 |
| 3,696,631 | 10/1972 | Valdes | 62/282 |
| 3,942,334 | 3/1976 | Pink | 62/266 |
| 4,124,992 | 11/1978 | Chmiel | 62/74 |
| 4,199,022 | 4/1980 | Senkan et al. | 165/2 |
| 4,304,293 | 12/1981 | Scheiwe et al. | 62/78 |
| 4,314,459 | 2/1982 | Rivoire | 62/51.1 |
| 4,340,263 | 7/1982 | Webb | 312/266 |
| 4,480,682 | 11/1984 | Kaneta et al. | 165/14 |
| 4,531,373 | 7/1985 | Rubinsky | 62/63 |
| 4,627,799 | 12/1986 | Terauchi | 418/55.4 |
| 4,656,006 | 4/1987 | Assmann et al. | 422/65 |
| 4,678,752 | 7/1987 | Thorne et al. | 422/65 |
| 4,681,839 | 7/1987 | Swartz | 435/1 |
| 4,712,607 | 12/1987 | Lindemans et al. | 165/30 |
| 4,713,941 | 12/1987 | Toyoda et al. | 62/48.3 |
| 4,751,184 | 6/1988 | Higo et al. | 422/65 |
| 4,790,141 | 12/1988 | Glascock | 62/78 |
| 4,870,829 | 10/1989 | Oullette | 62/51.1 |

*Primary Examiner*—Ronald C. Capossela
*Attorney, Agent, or Firm*—R. Neil Sudol; Henry D. Coleman

[57] ABSTRACT

A method used in low temperature storage of biological specimens comprises the steps of (a) maintaining a multiplicity of biological specimens within a predetermined low temperature range in a cryogenic storage unit, (b) selecting at least one biological specimen for removal from the storage unit, (c) determining a respective thaw period and thaw rate for the selected specimen, (d) automatically retrieving the selected specimen from the storage unit at removal time in accordance with the respective determined thaw period, and (e) automatically thawing the selected specimen at the respective thaw rate. An associated thawing system comprises a storage unit for maintaining a plurality of biological specimens within a predetermined low temperature range, a plurality of thawing chambers, and a heat exchange assembly for implementing a temperature change in each of the chambers independently of temperature changes in the other chambers. A servomechanism is provided for retrieving selected specimens from the storage unit and transfering the retrieved specimens to respective thawing chambers, while a control unit is operatively connected to the heat exchange assembly and the servomechanism for operating the heat exchange assembly to control rates of temperature changes in the thawing chambers and for activating the servomechanism to transfer the selected specimens from the storage unit to the respective chambers.

25 Claims, 13 Drawing Sheets

METHOD AND APPARATUS FOR USE IN LOW-TEMPERATURE STORAGE

BACKGROUND OF THE INVENTION

This invention relates to a method and apparatus for use in low-temperature storage More particularly, this invention relates to an apparatus with components for facilitating thawing of frozen specimens and further relates to an associated method. This invention also relates to a method and apparatus for facilitating the preparation of specimens for cryogenic storage.

U.S. Pat. No. 4,969,336 to Hermann Knippscheer et al. describes and claims a cryogenic storage apparatus wherein specimens in vials are individually inserted into and retrieved from a low-temperature storage unit. Identifying information relating to each individual specimen is entered into a computer which tracks the locations of the specimens along a snaking conveyor path inside the storage unit. The computer is thereby enabled to withdraw selected specimens upon request.

It is known that different kinds of biological tissues require different freezing and thawing protocols, i.e., different rates of temperature change and different lengths of intervals over which freezing and thawing are to occur. Sometimes different kinds of specimens are to be retrieved from storage and made available for research or other uses at the same time. However, the existence of different optimal thawing protocols necessitates substantial coordinating efforts to ensure that all specimens attain an effectively thawed out state at approximately the same time.

OBJECTS OF THE INVENTION

An object of the present invention is to provide a method and apparatus for facilitating the thawing of biological specimens.

A more particular object of the present invention is to provide such a method and apparatus for facilitating thawing of a plurality of biological specimens having different optimal thawing rates and times.

Another object of the present invention is to provide a method and apparatus for facilitating the freezing of biological specimens, even where the specimens have different optimal freezing rates and times.

Yet another object of the present invention is to provide a method and apparatus for essentially automatically thawing a plurality of biological specimens having different optimal thawing rates and times.

Another, more particular, object of the present invention is to provide such a method and apparatus wherein thawing of a plurality of such specimens occurs over at least partially overlapping intervals.

A further particular object of the present invention is to provide such a method and apparatus wherein a plurality of biological specimens having different optimal thawing rates and times are subjected to respective heating or warming operations so that the different specimens are available for use at approximately the same time.

An additional object of the present invention is to provide an apparatus for both freezing and thawing a plurality of specimens having different freezing and thawing protocols.

SUMMARY OF THE INVENTION

A method used in low temperature storage of biological specimens comprises, in accordance with the present invention, the steps of (a) maintaining a multiplicity of biological specimens within a predetermined low temperature range in a cryogenic storage unit, (b) selecting at least one biological specimen for removal from the storage unit, (c) determining a respective thaw period and a respective thaw rate for the selected specimen, (d) automatically retrieving the selected specimen from the storage unit at a removal times in accordance with the respective determined thaw period, and (e) automatically thawing the selected specimen at the respective thaw rate.

Pursuant to another feature of the present invention, the step of determining a thaw period and a thaw rate is implemented at least partially automatically. Preferably, the step of determining the thaw period and thaw rate includes the step of operating a general purpose computer to determine an optimal thaw period and an optimal thaw rate for the selected specimen, the computer being preprogrammed to store in digitally encoded form a table of pre-established thawing protocols for different kinds of specimens. Thus, the step of determining thaw periods and thaw rates includes the step of accessing a table of pre-established thawing protocols to determine optimal thaw periods and rates for selected specimen.

Pursuant to a further feature of the present invention, the step of thawing includes the steps of depositing a selected specimen in a respective thawing chamber and operating the thawing chamber to warm the specimen at the respective determined rate.

Pursuant to another feature of the present invention, the method further includes the step of automatically determining the removal times of a plurality of selected specimens in accordance with respective determined thaw periods, so that the selected specimens attain a thawed out state at approximately the same time.

A low-temperature storage system comprises, in accordance with the present invention, a storage unit for maintaining a plurality of biological specimens within a predetermined low temperature range, a plurality of thawing chambers, and a heat exchange assembly for implementing a temperature change in each of the chambers independently of temperature changes in the other chambers. A servomechanism is provided for retrieving a selected specimen from the storage unit and transfering the retrieved specimen to a respective thawing chamber, while a control unit is operatively connected to the heat exchange assembly and the servomechanism for operating the heat exchange assembly to control rates of temperature change in the selected thawing chamber and for activating the servomechanism to transfer the selected specimen from the storage unit to the respective chamber.

Pursuant to another feature of the present invention, the control unit includes a timer for triggering retrieval of the selected specimen from the storage unit at a time in accordance with a respective pre-established thawing protocol for the selected specimen Preferably, the control unit is preprogrammed with a plurality of thawing protocols in encoded form and automatically selects from among the stored thawing protocols in accordance with specimen type. A selector such as a keyboard is operatively connected to the control unit for inputting data into the control unit identifying the selected specimen.

Pursuant to additional features of the present invention, the storage unit includes a housing and a conveyor for moving the specimens along a predetermined path inside the housing. The control unit also includes a tracking device operatively linked to the conveyor for monitoring locations of specimens during motion thereof along the path under action of the conveyor. The storage unit may further include a verification device for automatically verifying the identity of the selected specimen upon retrieval thereof from the housing by the servomechanism.

A system operating in accordance with the present invention automatically thaws frozen biological specimens. A plurality of biological specimens having different optimal thawing protocols may be thawed without human intervention. Accordingly, several specimens may be automatically thawed over night, even though the specimens have different optimal thawing times and different optimal thawing rates. The system automatically retrieves selected specimens at the prespectively appropriate times and enters into a respective thawing schedule appropriate for each individual specimen.

Another low-temperature storage system in accordance with the present invention comprises a storage unit for maintaining a plurality of biological specimens within a predetermined low temperature range, a plurality of freezing chambers, and a cooling assembly for implementing a temperature change in each of the chambers independently of temperature changes in the other chambers. A servomechanism is provided for retrieving a predetermined specimen from a respective selected one of the chambers and transfering the retrieved specimen to the storage unit. A control unit is operatively connected to the cooling assembly and the servomechanism for operating the cooling assembly to control a rate of temperature change in the selected freezing chamber and for activating the servomechanism to transfer the predetermined specimen from the selected freezing chamber to the storage unit.

As discussed hereinabove with respect to a thawing embodiment of the invention, the storage unit includes a housing and a conveyor for moving the specimens along a predetermined path inside the housing, and the control unit includes a tracking mechanism operatively linked to the conveyor for monitoring locations of specimens during motion thereof along the path under action of the conveyor.

Preferably, the control unit includes a timer for triggering retrieval of the frozen specimen from the selected freezing chamber at a time in accordance with a respective preestablished freezing protocol for the specimen.

Pursuant to a further feature of the present invention, the control unit is preprogrammed with a plurality of freezing protocols in encoded form and includes means for automatically selecting from among the freezing protocols in accordance with specimen type.

A related method useful in low temperature storage of biological specimens in accordance with the present invention comprises the steps of (i) depositing a biological specimen in a freezing chamber, (ii) determining a freezing period and at least one freezing rate for the deposited specimen, (iii) automatically retrieving the deposited specimen from the freezing chamber at a removal time in accordance with the respective determined freezing period, (iv) automatically transfering the retrieved specimen from the freezing chamber to a cryogenic storage unit, and (v) storing the transfered specimen together with a multiplicity of other specimens in the cryogenic storage unit.

Pursuant to another feature of the present invention, the step of determining the freezing period and the freezing rate is implemented at least partially automatically. Specifically, the step of determining the freezing period and the freezing rate includes the step of operating a general purpose computer to determine the freezing period and the freezing rate, the computer being preprogrammed to store in digitally encoded form a table of pre-established freezing protocols for different kinds of specimens.

DETAILED DESCRIPTION

Figure 1:
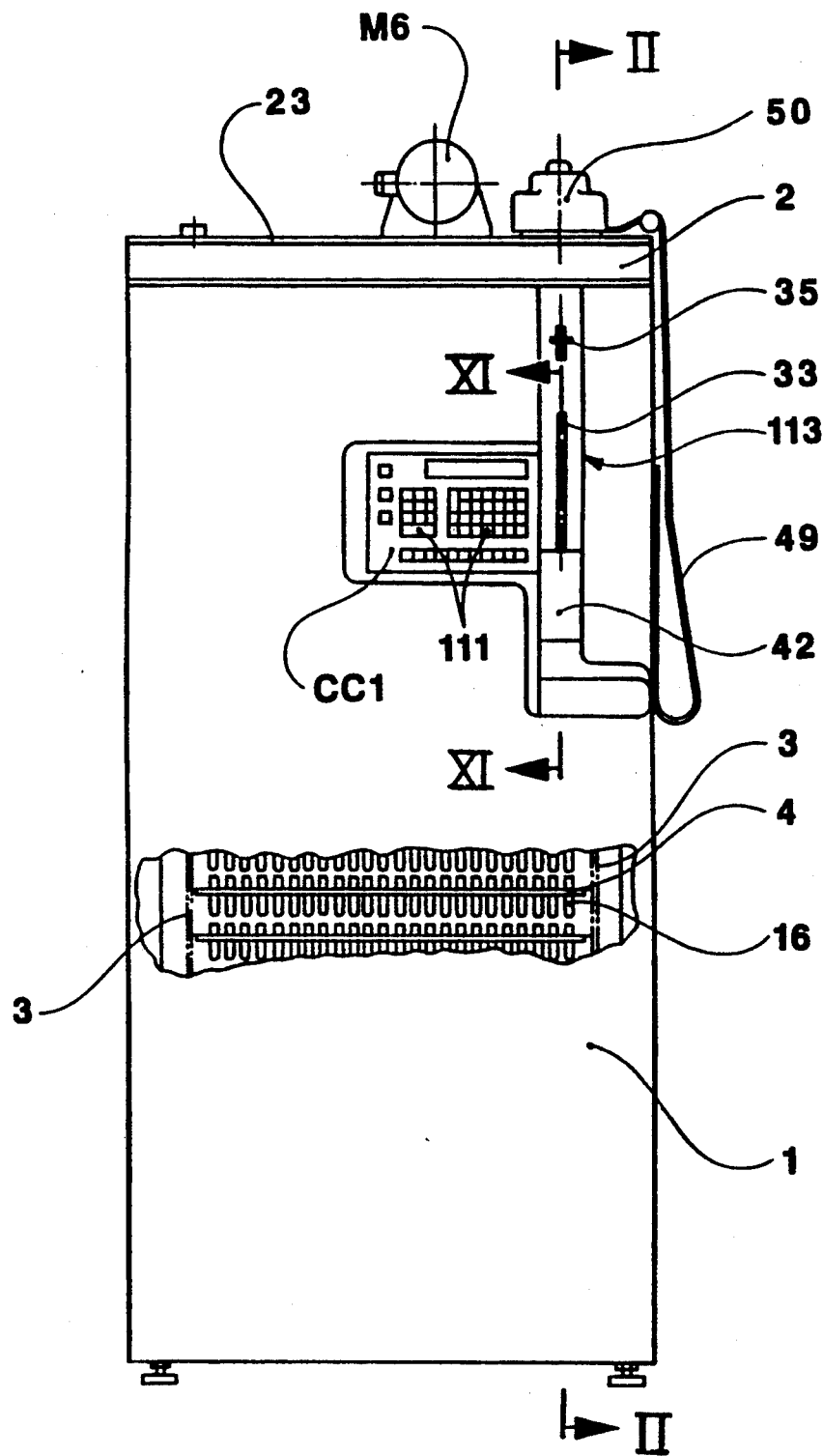
FIG. 1 is a front elevational view of a cryogenic storage apparatus useful in a cyrogenic system in accordance with the present invention.
Figure 2:
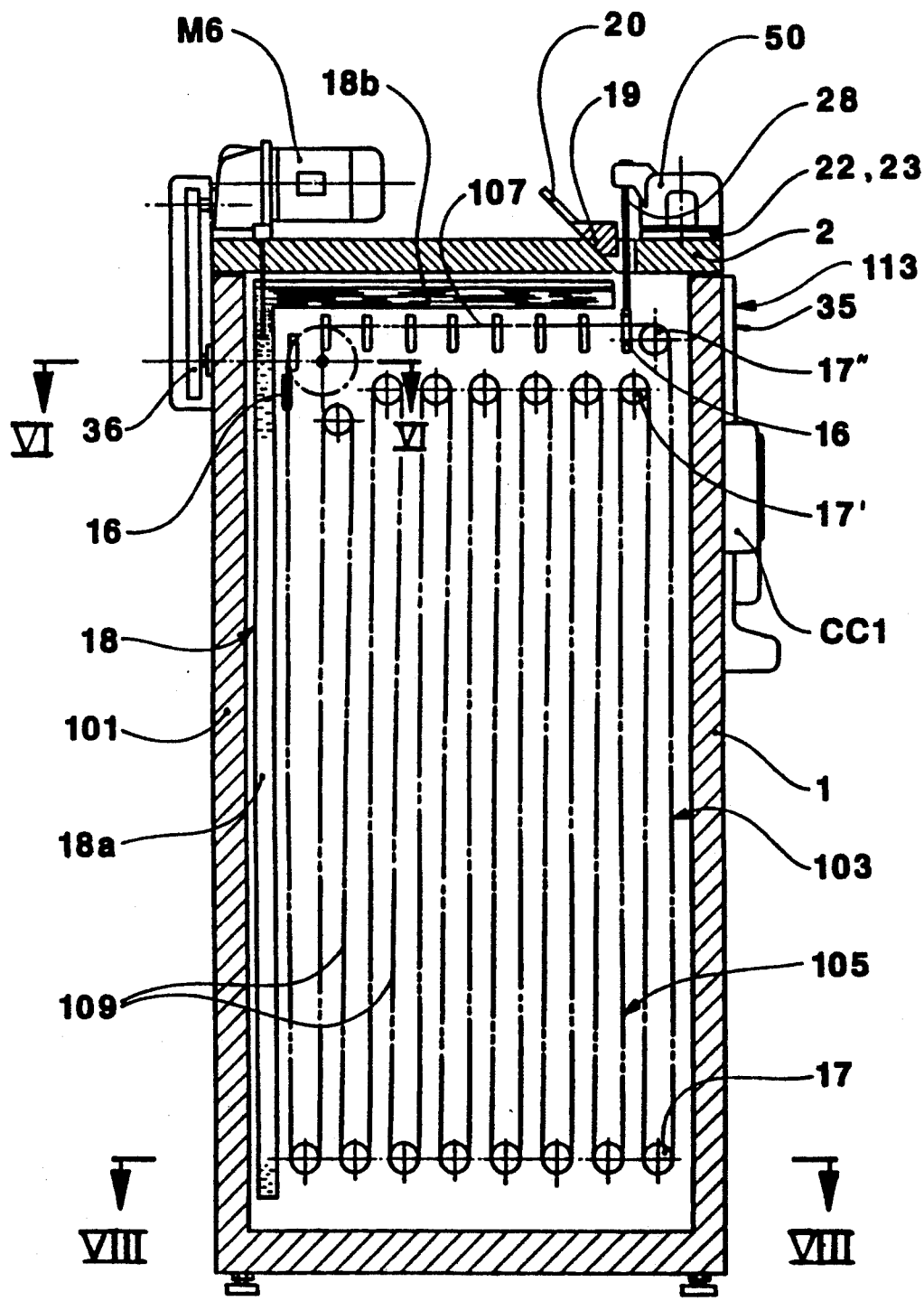
FIG. 2 is a schematic cross-sectional view taken along line A—A in FIG. 1.

As illustrated in FIGS. 1 and 2, a cryogenic storage apparatus for maintaining ampules or receptacles 16 at a substantially uniform low temperature approximately at the temperature of liquid nitrogen comprises a housing 1 with a lid or cover 2.

Ampules 16 are loaded into and retrieved from housing 1 automatically under the control of a microprocessor or computer CC1 mounted to housing 1 on a side wall thereof. The insertion and withdrawal of individual ampules is accomplished without exposure of the other specimen-containing ampules in housing 1 to ambient room-temperature air.

The cryogenic storage apparatus illustrated in FIGS. 1 and 2 will store approximately 8,000 ampules, each containing a respective specimen or sample.

Housing 1 defines a prismatic storage chamber which can be partially or totally filled with liquid nitrogen or a low-temperature gas. In the latter case, the gas is maintained at a low temperature by a minimal amount of liquid nitrogen held in a specially designed container 18 (FIG. 2). Container 18 preferably has an L-shaped cross-section with vertically extending leg 18a and a horizontally oriented leg 18b communicating with one another. Vertical leg 18a extends parallel and proximate to a side wall 101 of housing 1, while horizontal leg 18b is disposed near cover or upper wall 2 of the housing. Vertical leg 18a is provided on one side with a multiplicity of cooling fins which may engage side wall 101, while horizontal leg 18b is open along an upper side. The shape and location of container 18 are designed to achieve a temperature balance within housing 1 by virtue of radiant and gravitational cooling.

Figure 3:
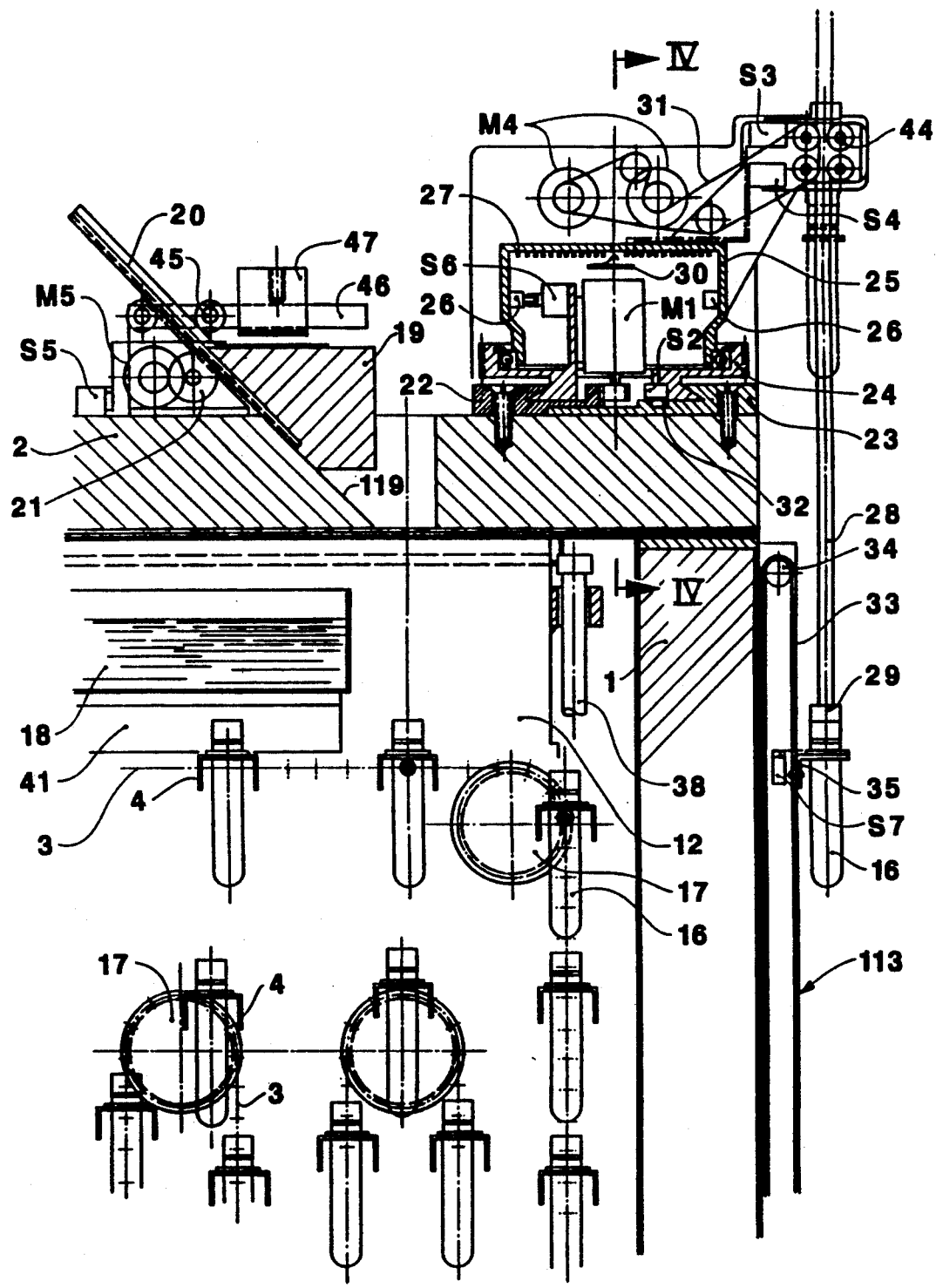
FIG. 3 is an enlarged, detail view ("Detail A") of the upper right hand corner of FIG. 2.

As shown in FIGS. 1 and 3, pluralities of ampules 16 are held on respective support bars 4 extending between and pivotably connected at their ends to a pair of endless conveyor chains 3. As shown in FIG. 2, chains 3 define a travel path 103 for the ampules through the housing chamber, the travel path having a lower snaking portion 105 and an upper portion 107 extending horizontally parallel to cover 2. Snaking portion 105 includes a plurality of vertically extending folds 109.

The position of each ampule 16 along path 103 is tracked in part by computer CC1. The computer memorizes the positions of all the ampules and updates the positions continuously during the motion of conveyor chains 3. In response to a selection made by an operator via a keyboard 111 (FIG. 1) of computer CC1, the computer controls the movement of chains 3 to position the selected ampule directly below an access door 19 in cover 2 (see FIGS. 2 and 3).

The snake-like alternating up and down movements of bars 4 and ampules 16 supported thereby contributes to the achievement of a gravitational temperature balance throughout the storage unit, in the case that coolant container 18 is being utilized.

The processes and devices for storing the liquid nitrogen outside housing 1, feeding it to container 18 and insulating housing 1 are well known in the art and are not further described herein.

The material of housing 1, container 18 and other components of the cryogenic storage apparatus, if not specifically set forth elsewhere herein, is preferably stainless steel or another substance suitable for long-term exposure to liquid nitrogen.

As illustrated in FIGS. 1-3, 11 and 12, the cryogenic storage apparatus is provided with an ampule lifting device 113 comprising a conveyor belt 33, pulleys 34 and motors M3 and their supports. The lifting device is particularly advantageous in the case that the height of housing 1 is so great that the ampule, when resting with an insulated enclosure or intermediate storage unit 142, is not easily accessible by an ampule insertion and extraction or retrieval mechanism 50 disposed on cover 2.

Motors M1 through M5 are duplex drives, each working motor being paired with an auxiliary back-up motor as a safety or precautionary measure. In the event that a primary, working motor should fail, the auxiliary motor will take over automatically and an audio visual signal will be generated, alerting an operator to initate immediate maintenance and repair procedures.

Figure 5:
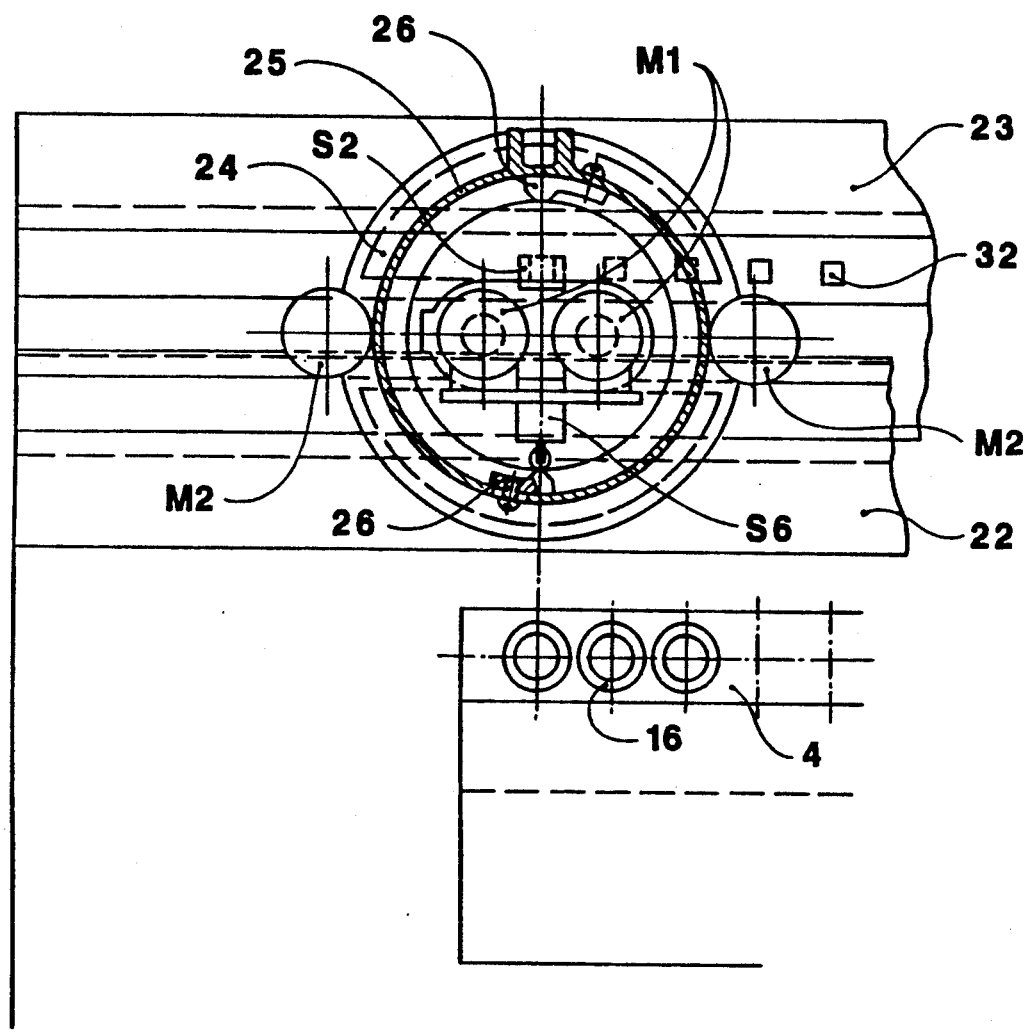
FIG. 5 is a partial cross-sectional view taken along line C—C in FIG. 4.

As illustrated in FIG. 3, support bars 4 have U-shaped transverse cross-sections. As best seen in FIGS. 1, 5 and 7, ampules 16 rest side by side on bars 4. Endless conveyor chains 3 are driven by a chain drive mechanism 115 (FIGS. 6 and 7) including sprockets 5 (FIG. 6) and 6 (FIG. 7) over idler pulleys 17 (FIGS. 3, 8 and 9) absolutely simultaneously along path 103 at a very low speed through the housing chamber. Bars 4 are fastened to chains 3 at spaced locations distanced to enable a free movement and vertical self-alignment of the bars and the ampules held thereby.

Figure 6:
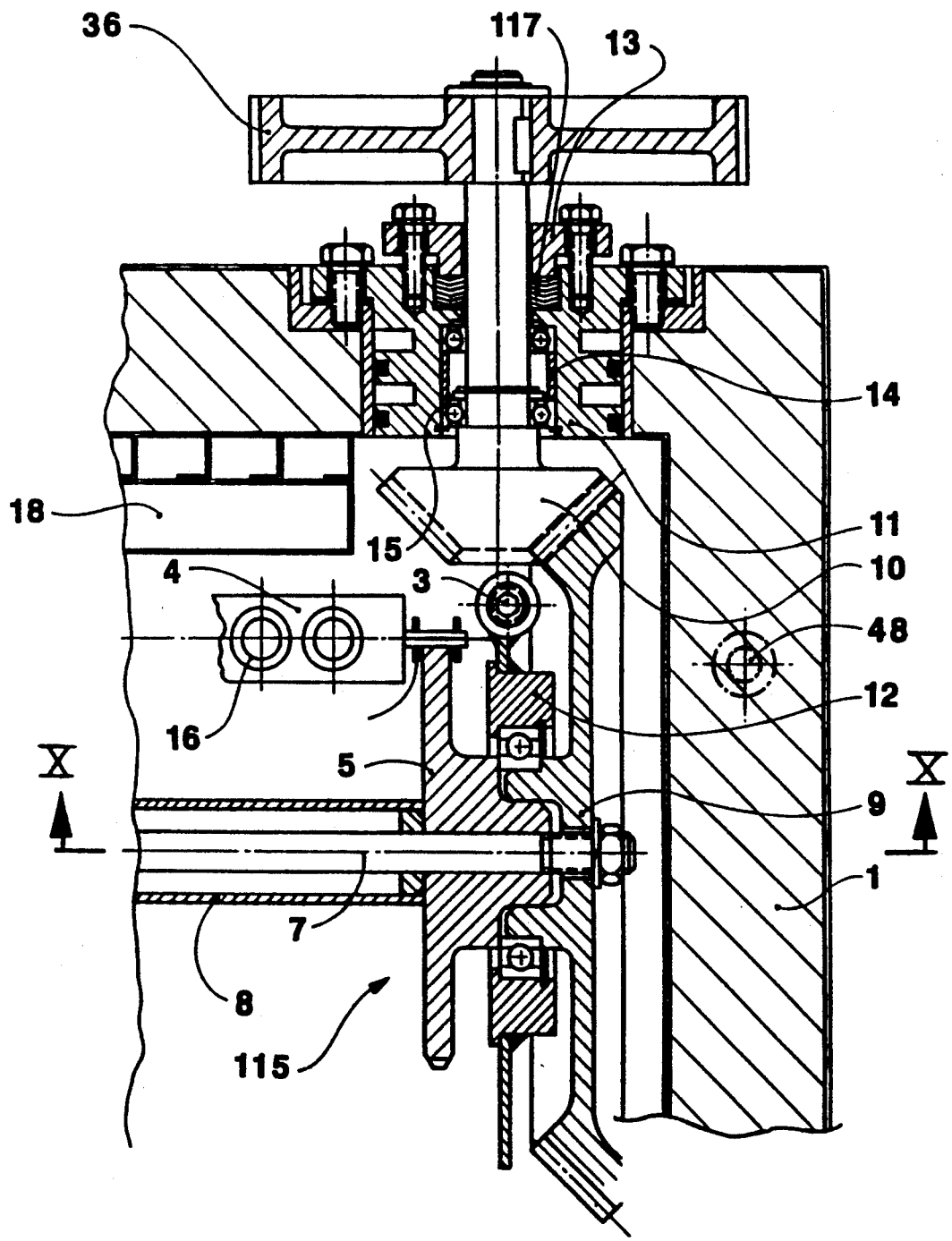
FIG. 6 is a cross-sectional view taken along line D—D in FIG. 2, showing a chain drive gear assembly.
Figure 7:
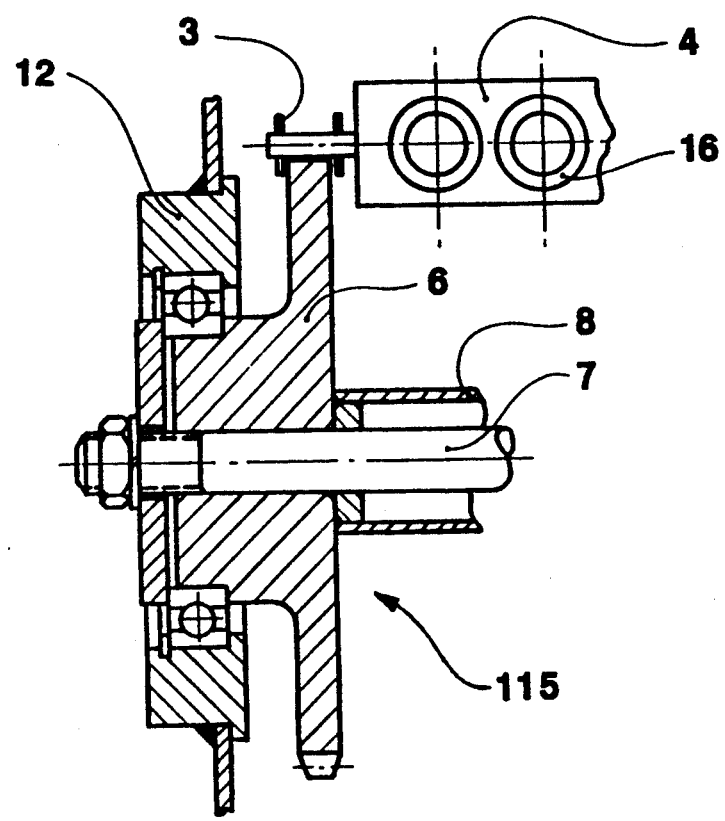
FIG. 7 is a cross-sectional view of a driving gear opposite a gear shown in FIG. 6.
Figure 10:
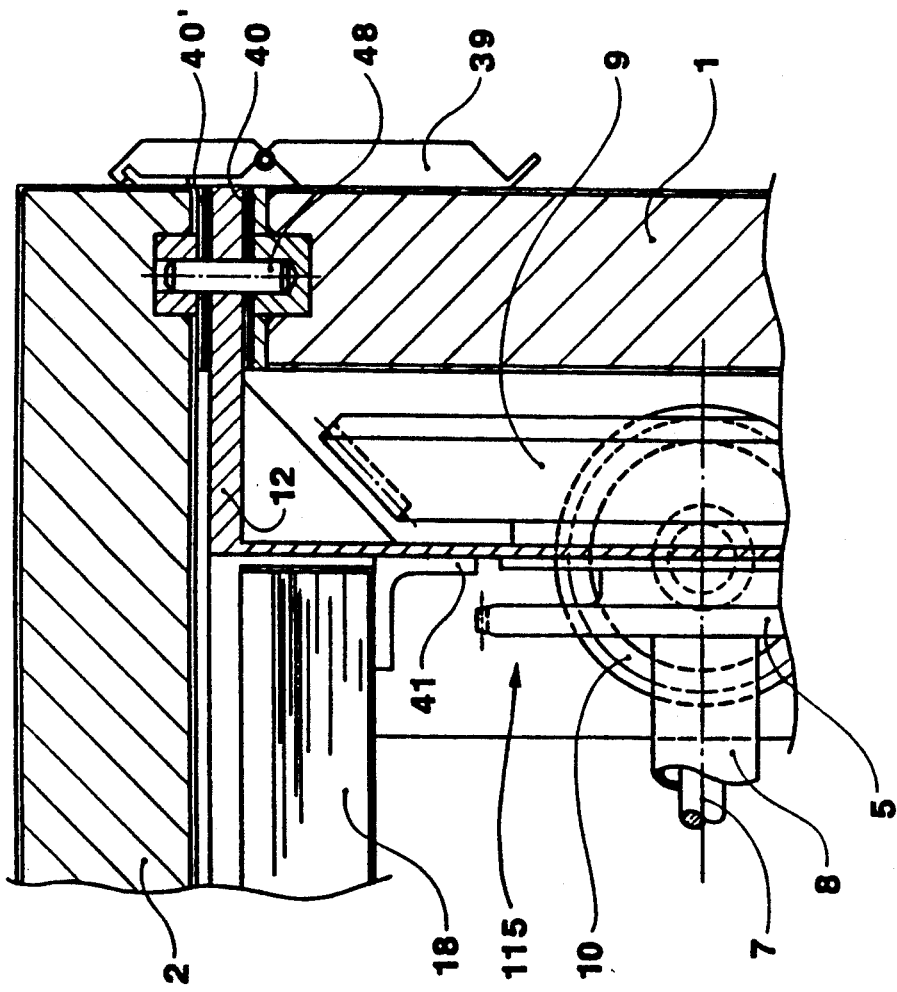
FIG. 10 is a partial cross-sectional view taken along line H—H in FIG. 6.

As depicted in FIGS. 6, 7 and 10, sprockets 5 and 6 of chain drive mechanism 115 are tightened against a spacer 8 by a spindle 7 and are driven by bevel gears 9 and 10. Bevel gear 10 is rotatably supported via roller bearings 15 and a distance sleeve 14 in a bearing casing II. Driving mechanism 115 is sealed by a stuffing box 13 with graphite packing 117. The bevel gear assembly illustrated in FIG. 6 is designed to be removed and maintained easily and quickly.

Bevel gears 9 and 10 of driving mechanism 115 are powered by a motor M6 disposed on the top and rear portion of cover 2. Motor M6 is operatively connected to bevel gears 9 and 10 via a toothed belt drive 36 (FIGS. 2 and 6).

Figure 8:
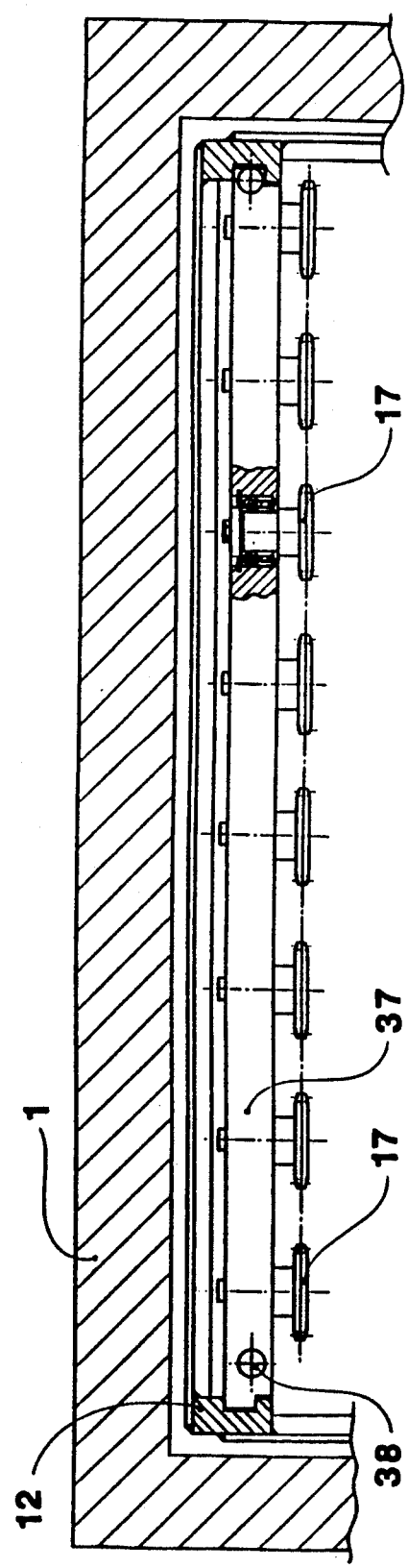
FIG. 8 is a partial cross-sectional view taken along line E—E in FIG. 2, illustrating a chain tensioning mechanism.
Figure 9:
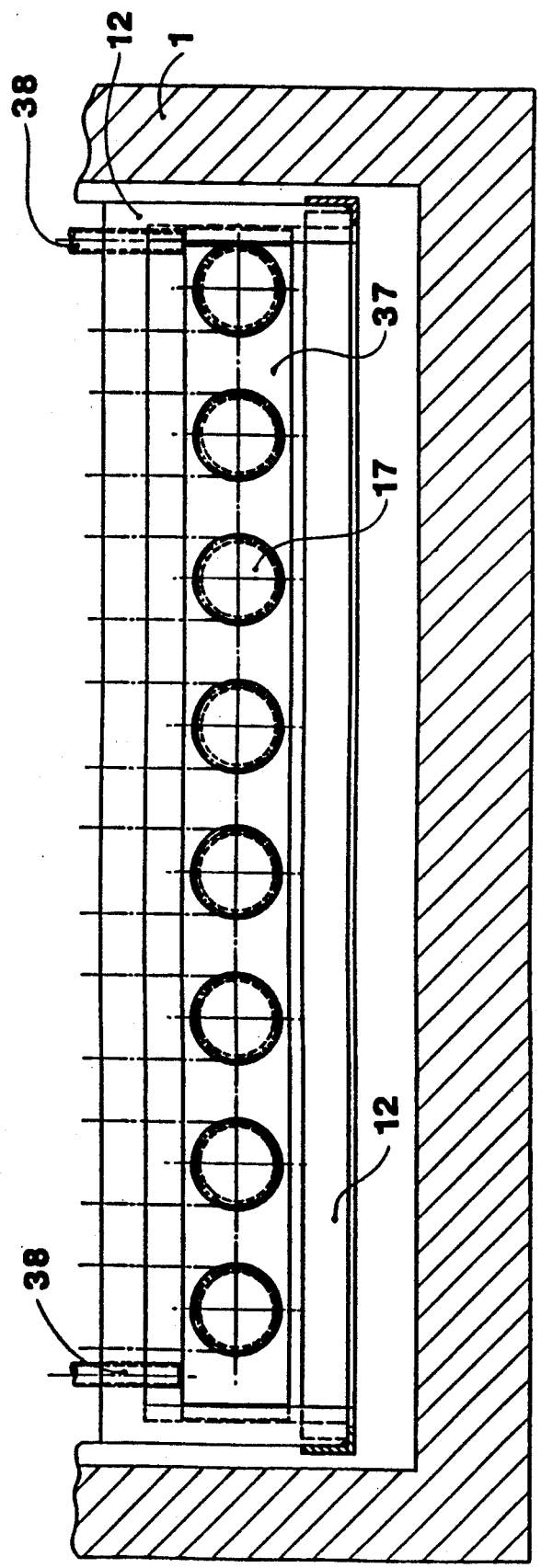
FIG. 9 is an elevational view of the chain tensioning mechanism of FIG. 8, taken from the bottom in that drawing figure and, as in FIG. 8, showing in cross-section a portion of a housing of the cryogenic storage apparatus.

As illustrated in FIGS. 2, 8 and 9, each endless conveyor chain 3 is partially wound over idler pulleys 17 and 17' rotatably mounted to inner frame structure 12 in two linear arrays at the top and the bottom of the housing. In addition, each conveyor chain 3 is partially wound about a further idler pulley 17" which serves to define horizontal chain portion 107.

Pulleys 17 of the lower rows are rotatably supported on opposite sides of an inner frame structure 12 by a bearing member 37 engineered to function as a chain tensioning device. Two long screws 38 on each side of frame structure 12 (FIGS. 3, 6, 8 and 9) push the bearing member down to tighten chains 3.

Frame structure 12 rests not on the bottom of housing 1 but is rather supported from the upper rim of the housing for facilitating adjustment of bevel gears 9 and 10 (FIG. 10). More particularly, frame 12 is secured to housing 1 via four alignment bolts 48 spaced around the perimeter of the upper rim of the housing. Aligning bolts 48 also aid in the alignment of cover 2 which is clamped to housing 1 by commercially available clamping levers 39 (see FIG. 10). Gaskets 40 and 40, are disposed between frame 12 and housing 1 and are made of graphite or other suitable insulating material.

As shown in FIG. 10, nitrogen container 18 is supported by brackets 41 from inner frame structure 12.

The process of depositing an ampule 16 into the cryogenic storage apparatus begins with the entry, into computer CC1 via keyboard 111, of a code number preassigned to the desired position of the ampule in the snaking array of support bars 4. Computer CC1 will compare the entered number with the numbers already in memory and verify the availability of the selected location. The code numbering system may simply take the form of a first set of consecutive numerals for successive bars 4 and a second set of consecutive numerals for adjacent ampule locations along a bar.

A tracking system is advantageously provided, exemplarily comprising computer CC1, together with an impulse module (not illustrated) on a driving shaft together with a decoder (not shown), both of which are commonly available. The decoder is operatively connected to computer CC1 for feeding thereto changes in the positions of endless conveyor chains 3, whereby the computer is at any time able to precisely locate the position of a given bar along path 103 within housing 1. Upon the selection of a particular ampule location (i.e., a specific bar 4 and a specific distance from one end of the bar), computer CC1 calculates the shortest direction of motion of chains 3 from the instantaneous position of the selected bar to access door 19 (FIG. 2) and will reverse the direction of chain drive, if necessary to minimize the search time.

Figure 11:
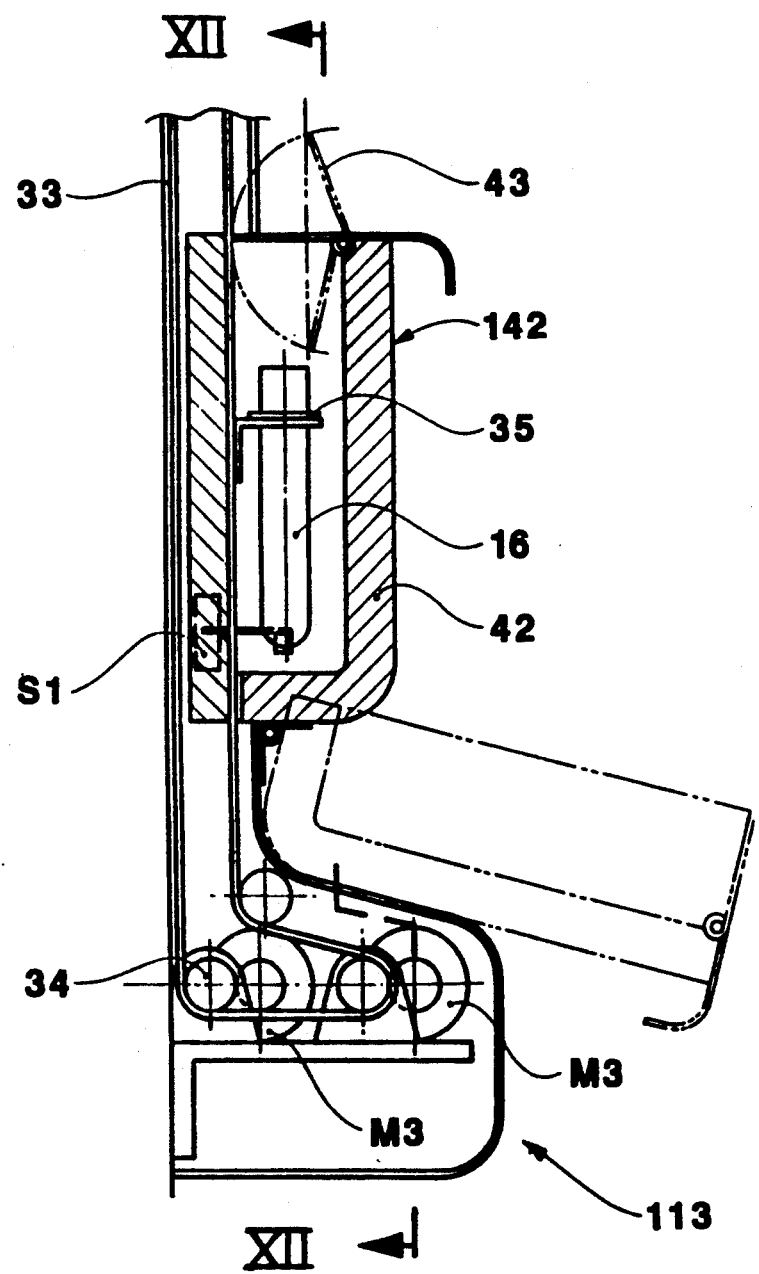
FIG. 11 is a partial cross-sectional view, on an enlarged scale, taken along line F—F in FIG. 1, depicting an intermediate storage container.
Figure 12:
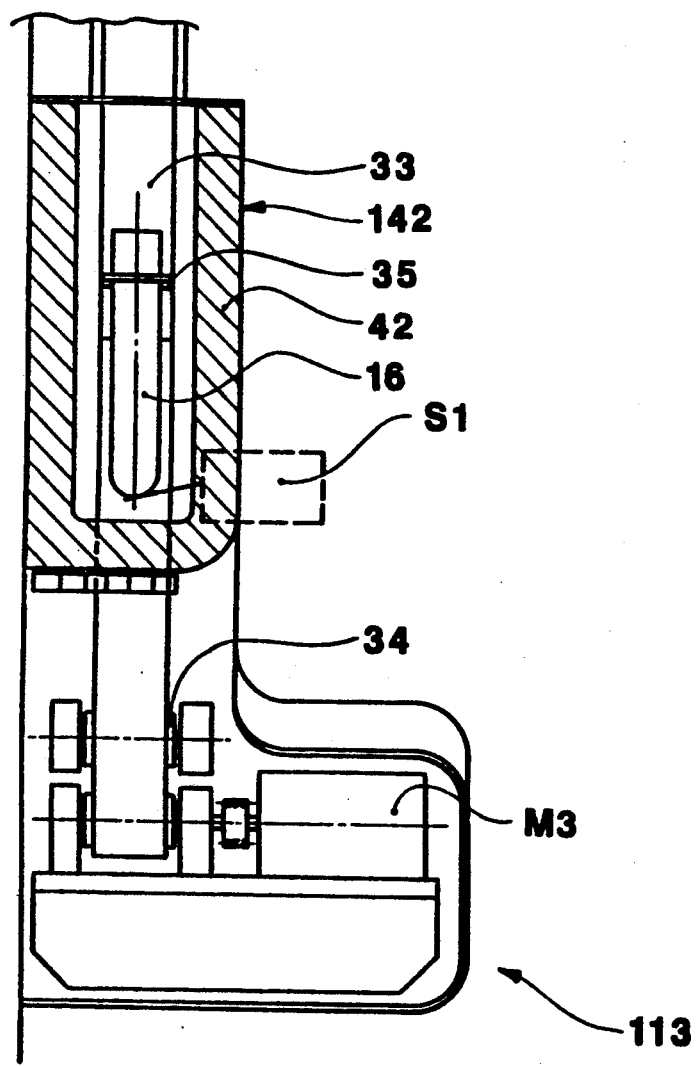
FIG. 12 is a partial cross-sectional view, on an enlarged scale, taken along line F—F in FIG. 11.

Further initial steps in the deposition of a specimen-containing ampule 16 in the cryogenic storage apparatus include the pivoting of an insulated cover member 42 of intermediate storage unit 142 from a closed position, illustrated in solid lines in FIG. 11, to an open position, shown in dot-dash lines. The ampule is then placed on a bracket member 35 attached to conveyor belt 33, cover member 42 being subsequently returned to the closed position. The ampule is now located temporarily inside a narrow insulated space of intermediate storage unit 142, enclosed by cover member 42 and by a spring loaded flap 43.

Upon placement of the ampule on bracket 35 (FIG. 11), a microswitch S1 signals computer CC1 that the ampule is ready to be deposited into the cryogenic storage apparatus. Computer activates lifting device 113 upon the arrival of the selected bar 4 precisely under door 19, which is closed at that stage of the ampule loading process. The activation of lifting device 113 consists in part of an energization of one of two motors M3 (see FIGS. 11 and 12) to drive conveyor belt 33 over pulleys 34 and thereby lift the ampule out from temporary storage inside intermediate storage unit 142 to a height determined by the location of a microswitch S7 (FIG. 3). Upon receiving a signal from microswitch S7, computer CC1 de-energizes the active motor M3, thereby halting the upward motion of the ampule.

While the ampule is being lifted from intermediate storage unit 142, ampule insertion and retrieval mechanism 50 is moved into a "zero" position, guided by dovetailed slide tracks 22 and 23 (FIG. 3) with a built-in gear track. Mechanism 50 is driven by a motor M1.

Motors M1, M2 and M4, switches S3, S4 and S6 and electromagnet 29 (FIG. 3) are supplied with power via a flat cable 49 (FIG. 1) extending from computer CC1 to ampule insertion and retrieval mechanism 50. Slide contacts 27 on a contact support 30 enable the transmission of electrical power to the motors, switches and electromagnet 29 of the ampule insertion and retrieval mechanism 50, even during rotation of an upper housing portion 25 thereof with respect to cover 2 of housing 1.

As illustrated in FIG. 3, electromagnet 29 is attached to a lower end of a spindle or rod 28 reciprocatingly driven by motor M4 via a belt 31 and grip rollers 44. Upon the reception of a signal from microswitch S7 and the subsequent arresting of conveyor belt 33, computer CC1 energizes motor M4 to shift rod 28 downwardly. Upon receiving a signal from microswitch S3, computer CC1 then deactivates motor M4, bringing the downward motion of rod 28 to a stop and energizes electromagnet 29 to form a magnetic link with a metal plate attached to the upper end of the ampule 16 held at the height of microswitch S7 by lifting device 113. The attachment of the metal plate on the ampule to the electromagnet closes a contact within the magnet, causing computer CC1 to again energize motor M4, this time in the reverse direction, to lift rod 28, together with the attached ampule. Upward motion of rod 28 is stopped by computer CC1 upon the reception thereby of a signal from microswitch S4.

As further depicted in FIG. 3, small magnets 32 are recessed into dovetailed side track or rail member 23 precisely at the location of the ampules on bars 4 within housing 1. Depending on the designated location at which the ampule carried by insertion and retrieval mechanism 50 is to be placed, microswitch S2 induces comuter CC1 to stop motor M1 and to activate two motors M5 (each of which is a member of a pair, an active motor and a backup). The activated motors M5 are located at opposite ends of access door 19, which extends substantially across the width of cover 2.

Motors M5 rotate respective pinions 21 which in turn translate respective racks 20 secured to door 19, whereby door 19 slides along a sloped surface 119 (FIG. 3) of cover 2 and opens access to the interior of housing 1. Door 19 is pushed against sloped surface 119 by rollers 45 which apply a torque to racks 20 and, consequently, wedge-shaped door 119 under the action of a lever arm 46 and an adjustable weight 47. Door 19 is self-aligning and self-sealing due to its-wedge-shaped cross section.

After microswitch S5 of the door opening and closing mechanism signals computer CC1 that door 19 has been opened, the computer stops motor M5 and also causes motor M2 of insertion and retrieval mechanism 50 to rotate upper housing portion 25 of the insertion and retrieval mechanism 180° around with the help of a ring gear which is part of dovetailed sliding carriage 21.

Two projecting pins 26 (FIGS. 3 and 5) connected to an inner surface of upper housing portion 25 of insertion and retrieval mechanism 50 cooperate with a microswitch S6 mounted to a sliding carriage member 24 of the insertion and retrieval mechanism to signal computer CC1 that rotation of 180° has been accomplished. The computer then deactivates motor M2 and simultaneously energizes motor M4 to lower rod 28, together with the ampule through the opened access door 19 and into the cooling chamber of the cryogenic storage apparatus.

Upon removal of an ampule from the cryogenic storage apparatus, a laser reader reads a bar code attached to the removed ampule to verify that the correct ampule has been retrieved. In the absence of verification, the retrieved ampule is returned immediately to housing 1 and an alarm signal is generated for alerting an operator as to the error. In addition, or alternatively, an alphanumeric code identifying the retrieved ampule may be displayed on a monitor connected to computer CC1. If verification occurs, the removal of the ampule proceeds normally.

Microswitch S3 then induces computer CC1 to stop motor M4 and the downward motion of rod 28 and to de-activate electromagnet 29, thereby enabling the deposition of the ampule into an aperture in the selected bar 4 at the selected position therealong. Opened contacts within electromagnet 29 then cause computer CC1 to lift rod 28 out of the housing through door 19. A subsequent signal from microswitch S4 leads to the arresting of the upward motion of the rod and causes computer CC1 to activate motors M5 to close door 19 and motor M6 to recommence continuous motion of bars 4 and their ampules 16 along path 103 through housing 1.

Figure 4:
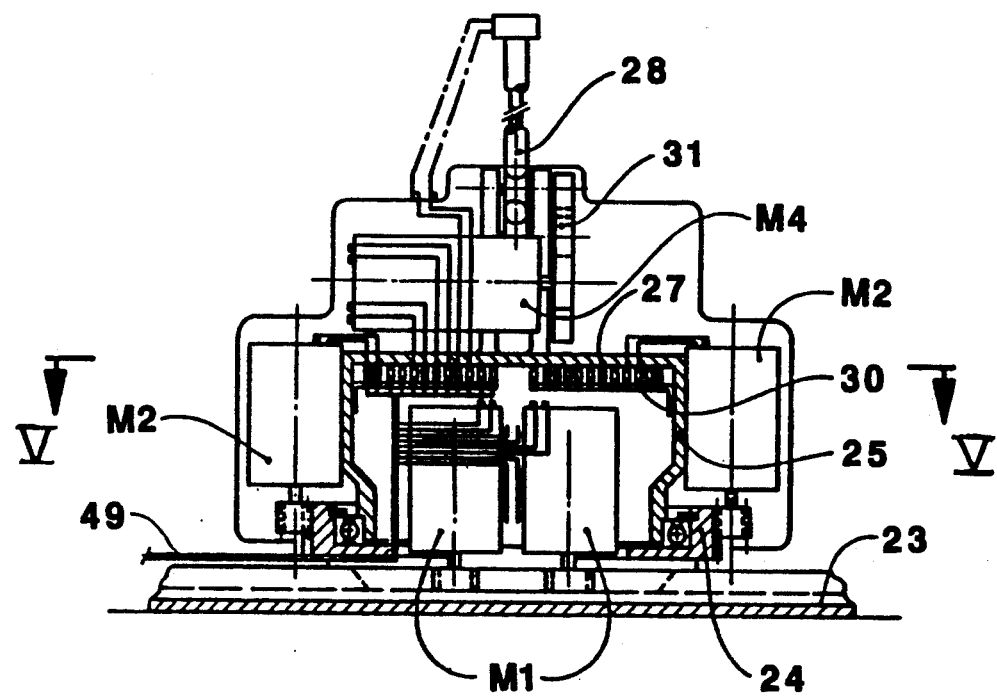
FIG. 4 is a partial cross-sectional view taken along line B—B in FIG. 3, showing a lifting mechanism.

As shown in detail in FIGS. 3 and 4, insertion and retrieval mechanism 50 includes dovetailed rail member 24 which is operatively fastened to cover 2 of housing 1 and extends parallel to door 19. Carriage 24 is slidably mounted to rail member 24 for motion therealong. Motor M1 (or its normally inactive backup) serves to move the carriage 24 along rail member 24 via a rack and pinion transmission assembly. Under the control of computer CC1, electromagnet 29 is raised and lowered by rod 28 to secure a hold on a selected ampule 16 positioned in housing 1 in juxtaposition to door 19.

Motors M4 serve to move rod 28 and electromagnet 29 a linear path through door 19. Upper housing portion 25 is rotatably mounted to carriage member 24, while motors M4 are mounted to housing portion 25. Rotary drive motors M2 (FIG. 4) are operatively connected to the rotatable housing portion for rotating the same relative to carriage member 24.

Figure 13:
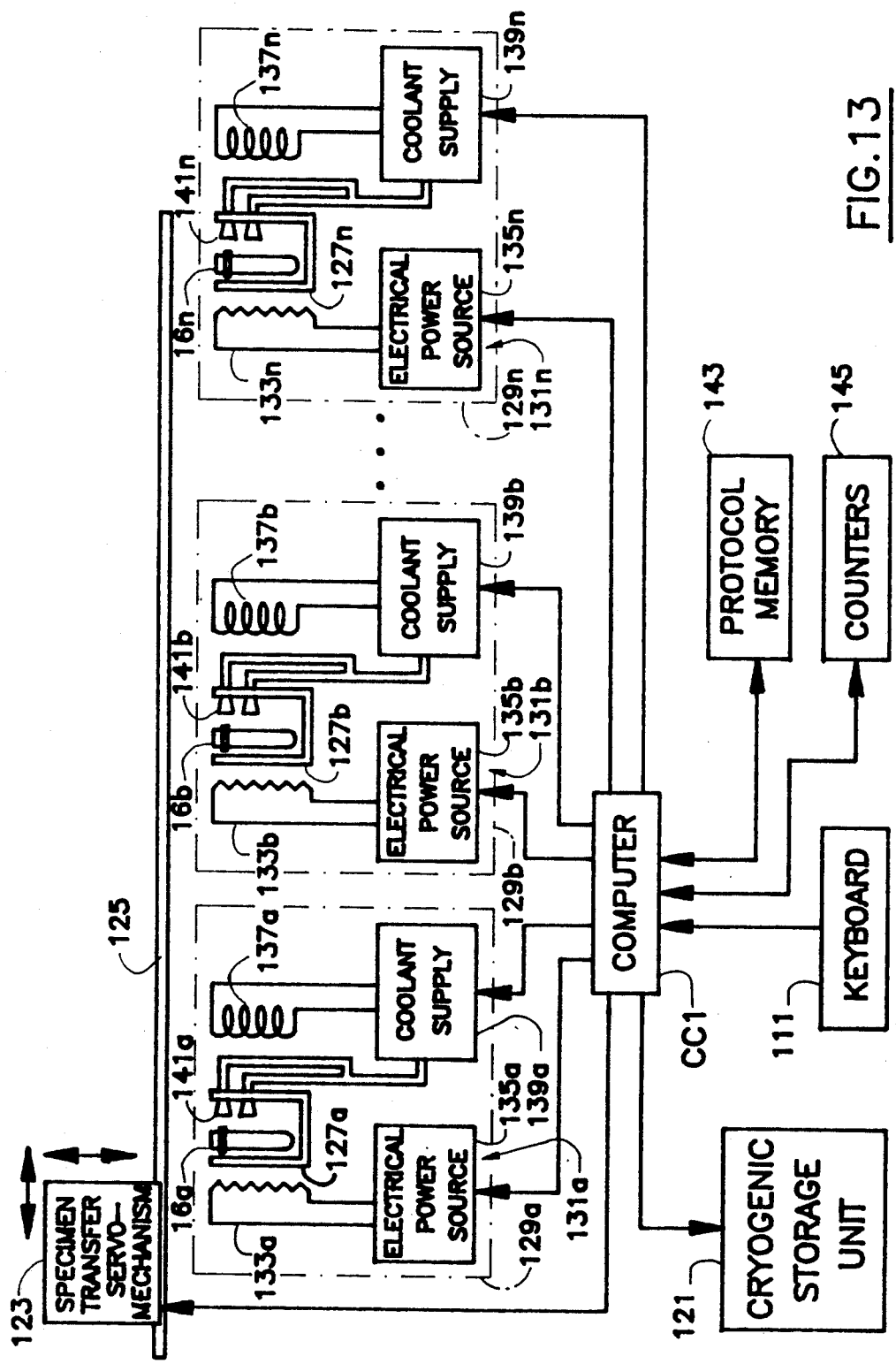
FIG. 13 is a block diagram of a cyrogenic storage system with automated thawing, in accordance with the present invention.

As illustrated in FIG. 13, a cryogenic storage system with automated thawing and freezing comprises a cryogenic storage unit 121 for storing a multiplicity of specimens. Preferably, storage unit 121 takes the form of the cyrogenic storage apparatus described hereinabove with reference to FIGS. 1-12. Storage unit 121 thus incorporates a conveyor assembly for moving a plurality of specimen-containing ampules along a snaking path past an automatically actuated door. Storage unit 121 further incorporates encoders for enabling computer CC1 to monitor or track the locations of the specimen-containing ampules within the storage unit. Storage unit 121 also includes a reservoir of liquid nitrogen or other cyrogenic substance and a servomechanism 123 (FIG. 13) for automatically inserting and retrieving individual specimens from the storage unit in response to signals from computer CC1. Servomechanism 123 may take the form of ampule insertion and extraction or retrieval mechanism 50 and rides along a rail 125 which extends from storage unit 121 past a plurality of thawing chambers 127a, 127b . . . 127n. Each thawing chamber 127a, 127b . . . 127n is part of a respective thawing unit 129a, 129b, . . . 129n which includes a respective heat exchange assembly 131a, 131b, . . . 131n for implementing a temperature change in each of the thawing chambers independently of temperature changes in the other chambers.

Each heat exchange assembly 131a, 131b, . . . 131n in turn includes a resistive heating circuit 133a, 133b, . . . 133n powered by a respective electrical source 135a, 135b, . . . 135n. Electrical power sources 135a, 135b, . . . 135n are controlled by computer CC1 to regulate the rates of warming of specimen-containing ampules 16a, 16b, . . . 16n placed in the respective thawing chambers 127a, 127b . . . 127n. Alternatively or additionally, each thawing unit 129a, 129b, . . . 129n includes a respective cooling circuit or coil 137a, 137b, . . . 137n fed with coolant from a supply or reservoir 139a, 139b, . . . 139n under the control of computer CC1. Coolant supplies 139a, 139b, . . . 139n may also be connected to respective sets of spray nozzles 141a, 141b, . . . 141n disposed in thawing chambers 127a, 127b, . . . 127n for spraying a bath of liquid coolant such as liquid nitrogen or a chlorofluorocarbon mixture from the respective supply onto the ampule 16a, 16b, . . . 16n being thawed.

The thawing of a specimen may be implemented, upon disposition of the specimen in an automatically preselected thawing chamber 127a, 127b, . . . 127n, by gradually decreasing the flow of coolant through the respective coil 137a, 137b, . . . 137n or through the respective nozzles 141a, 141b, . . . 141n at a rate predetermined by computer CC1 in accordance with a warming or thawing protocol or schedule selected from a memory 143 in accordance with the type of specimen. Accordingly, blood is thawed at a rate different from a more solid biological tissue. Optimal thawing rates, including successive different rates for certain materials, are known in the art, as demonstrated by the disclosure of U.S. Pat. No. 4,712,607 to Lindemans et al., the disclosure of which is hereby incorporated by reference.

As an alternative to decreasing the rate of coolant flow to provide a warming effect, specimen-containing ampules 16a, 16b, . . . 16n may be inserted into baths of coolant in the respective thawing chambers 127a, 127b, . . . 127n. The respective heating circuits 133a, 133b, . . . 133n are then energized at respective predetermined, possibly increasing, rates. Each such heating rate is predetermined by computer CC1 in accordance with thawing schedules or protocols stored in encoded form in memory 143 for the different kinds of biological specimens.

It is to be noted that the function of specimen-transfer servomechanism 123 may be accomplished by a plurality of robot mechanisms which transfer specimen-containing ampules to one another and then deposit the ampules into thawing chambers 127a, 127b, . . . 127n. It is to be noted further that thawing chambers may take any form known in the art. An appropriate form of thawing chamber is disclosed in U.S. Pat. No. 4,712,607. In accordance with that patent, power is supplied to a heat generating device whenever an actual, sensed, temperature falls below a desired temperature determined according to a temperature cycle stored in memory.

Thawing units 129a, 129b, . . . 129n may be used for freezing specimens by reversing the functioning of certain components. For example, the flow of coolant through coolant coils 137a, 137b, . . . 137n or through nozzles 141a, 141b, . . . 141n may be increased at rates predetermined by computer CC1 in accordance with freezing protocols or schedules selected from memory 143 in accordance with the type of specimen. Thus, computer CC1 may monitor and control freezing and thawing operations taking place simultaneously in different chambers 1227a, 127b, . . . 127n.

As illustrated in FIG. 13, control unit or computer CC1 is connected to a bank of counters or timers 145 for triggering retrieval of the selected specimens from the storage unit at different times in accordance with respective pre-established thawing protocols for the selected specimens. Counters or timers 145 may form an area within the memory banks of computer CC1.

Computer CC1 is preprogrammed with specimen thawing protocols in encoded form, i.e., the thawing protocols are stored in memory 143. Computer CC1 automatically selects from among the thawing protocols in accordance with specimen type. Typically, a selection made via keyboard 111 will identify a particular specimen and a time that the specimen is to be available in a thawed state. In response to that input, computer CC1 consults memory 143 (or an internal memory) and determines the type of biological material of the requested specimen. Computer CC1 then accesses memory 143 to determine such parameters of the thawing protocol as the total time required for warming and the rates of warming for that type of specimen. Computer CC1 then sets a timer in counter bank 145 to flag the time that the requested specimen is to be removed from storage unit 121.

Counters 145 thus alert computer CC1 as to times for initiating thawing procedures on selected specimens. Counters 145 may also be set by computer CC1 for flagging changes in warming rates, as well as for signaling the termination of thawing operations. Computer CC1 may activate an optional signaling device (not illustrated) to alert human operators that thawing has been completed for one or more selected specimens.

Upon determining that the time has arrived for commencing a thawing operation on a requested specimen, computer CC1 transmits control signals to storage unit 121 and servomechanism 123 to induce those components to extract the selected specimen from the storage unit and to transfer the retrieved specimen to a thawing chamber 127a, 127b, . . . or 127n selected by the computer. Computer CC1 selects the thawing chamber basically according to availability, but if the thawing chambers have different design specifications, for example, different thawing rate capabilities and capacities, then the selection can be implemented in accordance with more detailed information.

As discussed above, in order to control the warming of the retrieved specimen upon disposition thereof in the selected thawing chamber 127a, 127b, . . . 127n, computer CC1 activates the respective electrical power source 135a, 135b, . . . 135n and/or opens a valve in the respective coolant supply 139a, 139b, . . . 139n to thereby control the rate at which heat is provided to the thawing chamber. As pointed out above, the control of the thawing process may be implemented pursuant to the teachings of U.S. Pat. No. 4,712,607.

It is to be noted that computer CC1 may be controlling thawing cycles for several specimens simultaneously to ensure that all such specimens attain a desired thawed state at approximately the same time. Computer CC1 takes into account the different thawing protocols.

This result is advantageous, for example, in having a plurality of specimens thawed over night and ready for experimental research at the beginning of the work day.

As noted hereinabove, the apparatus illustrated in FIG. 13 is also utilizable for controlling the simultaneous or sequential freezing of a plurality of biological specimens. Computer CC1 first selects a freezing chamber from among chambers 127a, 127b, . . . 127n. The selection is made in accordance with the specimen type and other information entered into computer CC1 via keyboard 111. Sometimes the selection is arbitrary, depending only on availability of chambers 127a, 127b, . . . 127n.

Upon the selection of a freezing chamber from among chambers 127a, 127b, . . . 127n, computer CC1 activates seromechanism 123 to transfer the specimen to the selected chamber 127a, 127b, . . . or 127n. The specimen to be frozen is placed, for example, by hand into enclosure 142 and is then transfered by servomechanism 123 from enclosure 142 to the proper chamber 127a, 127b, . . . or 127n.

Prior to the commencement of freezing operations and preferably prior to placement of the specimen into the freezing chamber, computer CC1 accesses in memory 143 a table of freezing protocols, i.e., optimal freezing periods and associated freezing rates, for a multiplicity of specimen types. From that table, computer CC1 determines the optimal freezing period and rate or rates for the specimen to be frozen. Thus, the timing of subperiods having different freezing rates is determined by computer CC1 in accordance with freezing rate information from member 143 and is implemented by the computer with the aid of counters 145.

Upon deposition of the specimen into the selected freezing chamber 127a, 127b, . . . or 127n, computer CC1 activates the respective power source 131a, 131b, . . . or 131n and/or the respective coolant supply 139a, 139b, ... or 139n to control the rate of freezing of the specimen. More particularly, the rate of freezing may be controlled by modifying the rate of coolant flow through the respective coil 137a, 137b, . . . or 137n or out of the respective spray nozzle 141a, 141b, . . . or 141n. The rate of cooling may be finely tuned through the use of resistive heating circuits 133a, 133b, . . . 133n.

Upon termination of the cooling operation, as determined by computer CC1 from the freezing protocol information for the subject specimen and through the use of counters 145, or, alternatively or additionally, as determined by computer CC1 in response to temperature sensor data sensors (not shown), computer CC1 activates servomechanism 123 to remove the frozen specimen from the freezing chamber 127a, 127b, . . . or 127n and to transfer the frozen specimen to storage unit 121.

It is to be noted that the freezing chambers 127a, 127b, . . . 127n may take any form known in the art. Such chambers are disclosed in U.S. Pat. No. 4,712,607 and U.S. Pat. No. 4,304,293 to Scheiwe et al., the disclosure of which is hereby incorporated by reference.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A low-temperature storage system comprising:
   storage means for maintaining a plurality of biological specimens within a predetermined low temperature range;
   a plurality of thawing chambers;
   heating means for implementing a temperature change in each of said chambers independently of temperature changes in each other of said chambers;
   servomechanism means for retrieving a selected specimen from said storage means and transfering the retrieved specimen to a respective selected one of said chambers; and
   control means operatively connected to said heating means and said servomechanism means for operating said heating means to control a rate of temperature change in said selected one of said chambers and for activating said servomechanism means to transfer said selected specimen from said storage means to said selected one of said chambers.

2. The system defined in claim 1 wherein said storage means includes a housing and conveyor means for moving said specimens along a predetermined path inside said housing.

3. The system defined in claim 2 wherein said control means includes tracking means operatively linked to said conveyor means for monitoring locations of specimens during motion thereof along said path under action of said conveyor means.

4. The system defined in claim 2 wherein said storage means further includes verification means for automatically verifying the identity of said selected specimen upon retrieval thereof from said housing by said servomechanism means.

5. The system defined in claim 1 wherein said control means includes timing means for triggering retrieval of said selected specimen from said storage means at a time in accordance with a respective pre-established thawing protocol for said selected specimen.

6. The system defined in claim 5 wherein said control means is preprogrammed with a plurality of thawing protocols in encoded form and includes means for automatically selecting from among said thawing protocols in accordance with specimen type.

7. The system defined in claim 1, further comprising selection means operatively connected to said control means for inputting data into said control means identifying said selected specimen.

8. The system defined in claim 1, further comprising a plurality of freezing chambers and cooling means for implementing a temperature change in each of said chambers independently of temperature changes in each other of said chambers, said servomechanism means being operable for retrieving a predetermined specimen from a respective selected one of said freezing chambers and transferring the retrieved predetermined specimen to said storage means, said control means being operatively connected to said cooling means and said servomechanism means for operating said cooling means to control a rate of temperature change in said selected one of said chambers and for activating said servomechanism means to transfer said predetermined specimen from said selected one of said freezing chambers to said storage means.

9. The system defined in claim 8 wherein each of said thawing chambers and each of said freezing chambers is provided with both heating and cooling capability.

10. A method used in low temperature storage of biological specimens, comprising the steps of:
maintaining a multiplicity of biological specimens within a predetermined low temperature range in a cryogenic storage unit;
selecting at least one of said biological specimens for removal from said storage unit;
determining a thaw period and at least one thaw rate for the elected specimen;
automatically retrieving said selected specimen from said storage unit at a removal time in accordance with the respective determined thaw period; and
automatically thawing said selected specimen at the respective thaw rate, said step of thawing including the steps of automatically depositing said selected specimen in a thawing chamber and operating said thawing chamber to warm said selected specimen at the respective determined rate.

11. The method defined in claim 10 wherein said step of determining said thaw period and said thaw rate is implemented at least partially automatically.

12. The method defined in claim 11 wherein said step of determining said thaw period and said thaw rate includes the step of operating a general purpose computer to determine said thaw period and said thaw rate, said computer being preprogrammed to store in digitally encoded form a table of pre-established thawing protocols for different kinds of specimens.

13. The method defined in claim 11 wherein said step of determining said thaw period and said thaw rate includes the step of accessing a table of pre-established thawing protocols to determine an optimal thaw period and rate for the selected specimen.

14. The method defined in claim 10, further comprising the step of automatically determining removal times for a plurality of selected specimens from respective determined thaw periods, so that the selected specimens attains a thawed out state at approximately the same time.

15. The method defined in claim 10, further comprising the step of automatically moving said specimen along a predetermined path inside said storage unit.

16. The method defined in claim 15, further comprising the step of automatically tracking locations of specimens during motion thereof along said path.

17. The method defined in claim 15, further comprising the step of automatically verifying the identities of said selected specimen upon retrieval thereof from said storage unit.

18. A low-temperature storage system comprising:
storage means for maintaining a plurality of biological specimens within a predetermined low temperature range;
a plurality of freezing chambers;
cooling means for implementing a temperature change in each of said chambers independently of temperature changes in each other of said chambers;
servomechanism means for retrieving a predetermined specimen from a respective selected one of said chambers and transfering the retrieved specimen to said storage means; and
control means operatively connected to said cooling means and said servomechanism means for operating said cooling means to control a rate of temperature change in said selected one of said chambers and for activating said servomechanism means to transfer said predetermined specimen from said selected one of said chambers to said storage means.

19. The system defined in claim 18 wherein said storage means includes a housing and conveyor means for moving said specimens along a predetermined path inside said housing, and wherein said control means includes tracking means operatively linked to said conveyor means for monitoring locations of specimens during motion thereof along said path under action of said conveyor means.

20. The system defined in claim 18 wherein said control means includes timing means for triggering retrieval of said predetermined specimen from said selected one of said chambers at a time in accordance with a respective pre-established freezing protocol for said predetermined specimen.

21. The system defined in claim 20 wherein said control means is preprogrammed with a plurality of freezing protocols in encoded form and includes means for automatically selecting from among said freezing protocols in accordance with specimen type.

22. A method used in low temperature storage of biological specimens, comprising the steps of:
depositing a biological specimen in a freezing chamber;
determining a freezing period and at least one freezing rate for the deposited specimen;
automatically retrieving the deposited specimen from said freezing chamber at a removal time in accordance with the respective determined freezing period;
automatically transfering the retrieved specimen from said freezing chamber to a cryogenic storage unit; and
storing the retrieved and transfered specimen together with a multiplicity of other specimens in said cryogenic storage unit.

23. The method defined in claim 22 wherein said step of determining said freezing period and said freezing rate is implemented at least partially automatically.

24. The method defined in claim 23 wherein said step of determining said freezing period and said freezing rate includes the step of operating a general purpose computer to determine said freezing period and said freezing rate, said computer being preprogrammed to store in digitally encoded form a table of preestablished freezing protocols for different kinds of specimens.

25. The method defined in claim 23 wherein said step of determining said freezing period and said freezing rate includes the step of accessing a table of pre-established freezing protocols to determine an optimal freezing period and rate for the deposited specimen.

* * * * *